United States Patent
Evans et al.

(10) Patent No.: US 6,361,194 B1
(45) Date of Patent: Mar. 26, 2002

(54) HANDHELD ULTRAVIOLET INSPECTION LAMP

(75) Inventors: Michael S. Evans, Camden, MI (US); Howard Scott Ryan, Skaneateles, NY (US); Scott King, Pioneer, OH (US)

(73) Assignee: SPX Corporation, Muskegon, MI (US)

( * ) Notice: Subject to any disclaimer, the term of this patent is extended or adjusted under 35 U.S.C. 154(b) by 0 days.

(21) Appl. No.: 09/592,941

(22) Filed: Jun. 13, 2000

Related U.S. Application Data

(63) Continuation-in-part of application No. 29/113,136, filed on Oct. 29, 1999.

(51) Int. Cl.[7] .............................................. F21L 15/12
(52) U.S. Cl. ..................... 362/399; 362/199; 315/200 A
(58) Field of Search ................... 362/293, 264, 362/294, 343, 399, 486, 157, 158, 183–208, 197, 1; 250/77, 392, 393, 504; D26/37–50; 315/200 A

(56) References Cited

U.S. PATENT DOCUMENTS

| | | | |
|---|---|---|---|
| 2,613,313 A | 10/1952 | Weeks ........................ | 240/10.6 |
| 3,136,890 A | 6/1964 | Wain ............................ | 250/77 |
| D300,470 S | * 3/1989 | Schidt et al. ................. | D26/37 |
| D301,752 S | * 6/1989 | Osterhout ..................... | D26/37 |
| 5,050,055 A | * 9/1991 | Lindsay et al. .............. | 362/293 |
| D342,582 S | * 12/1993 | Young .......................... | D26/37 |
| 5,674,000 A | 10/1997 | Kalley ......................... | 362/293 |
| 5,742,066 A | 4/1998 | Cavestri ...................... | 250/504 |
| 5,788,364 A | 8/1998 | Cooper et al. .............. | 362/293 |
| 5,816,692 A | 10/1998 | Cooper et al. .............. | 362/293 |
| 5,905,268 A | 5/1999 | Garcia et al. ............... | 250/504 |
| 5,911,497 A | * 6/1999 | Mele ........................... | 362/202 |
| 5,997,154 A | * 12/1999 | Copper et al. .............. | 362/293 |
| D434,868 S | * 12/2000 | Trigiani ....................... | D26/37 |
| D434,989 S | * 12/2000 | Evans et al. ................. | D10/78 |

FOREIGN PATENT DOCUMENTS

GB      2 065 857      7/1981

* cited by examiner

*Primary Examiner*—Con Wong
*Assistant Examiner*—Trinh Vo Dinh
(74) *Attorney, Agent, or Firm*—Baker & Hostetler, LLP

(57) ABSTRACT

A handheld ultraviolet inspection lamp that has a housing with a grippable handle portion with a first finger indentation with an on/off trigger switch received within a recess therein, a bulb chamber portion with a filter lens, and a bulb assembly with a bulb and a reflector, the bulb assembly being positioned within the bulb chamber portion.

8 Claims, 6 Drawing Sheets

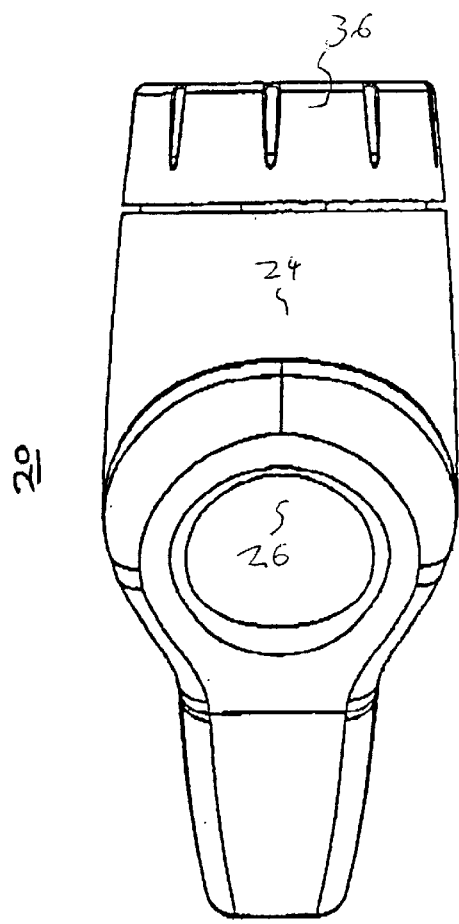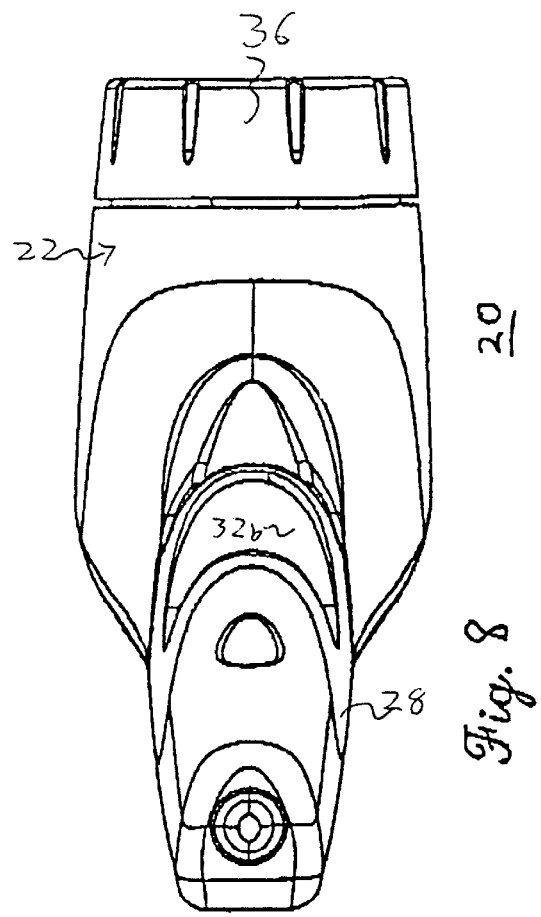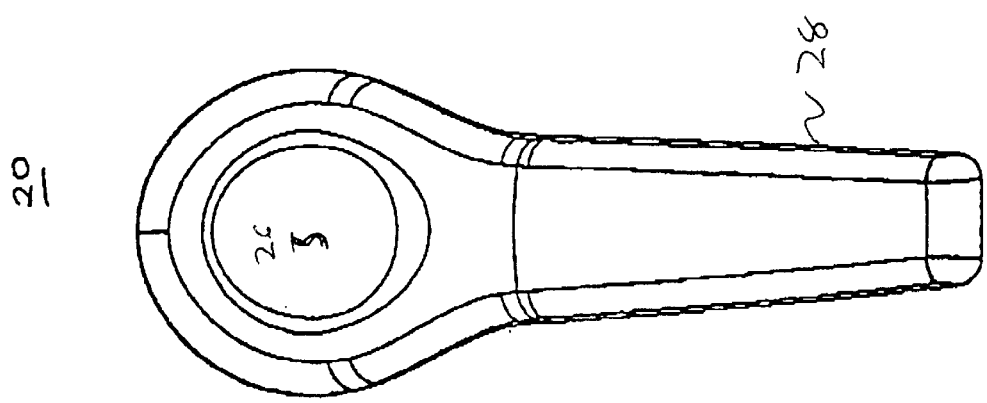

HANDHELD ULTRAVIOLET INSPECTION LAMP

CONTINUING INFORMATION

This application is a continuation-in-part of application Ser. No. 29/113,136 filed on Oct. 29, 1999, of which is hereby incorporated by reference in its entirety, including the drawings and the specification.

BACKGROUND OF THE INVENTION

1. Field of the Invention

The present invention relates to the field of inspection lamps for the detection of fluorescent materials, and in particular to the field of such lamps for use in vehicle diagnostics.

2. Description of Related Art

It is a well-known phenomena that electromagnetic radiation within the ultraviolet ("UV") spectrum produces fluorescence in certain materials. That is, the fluorescent materials absorb radiated energy at the UV wavelength and re-radiate it at a longer wavelength in the visible spectrum. This phenomena has enabled inspection and detection techniques in which fluorescent dyes, inks or paints are illuminated by lamps selectively filtered to emit only ultraviolet radiation (often called "black light" because little visible spectrum light escapes the filter), and then re-radiate with a high luminescence in the visible spectrum.

These techniques are used extensively in non-destructive testing, leak detection and security systems. For example, the slow leakage of refrigerant from an air conditioning system is difficult to locate by any other means, because the refrigerant escapes as an invisible gas at such low rate and rapid diffusion that the concentration of refrigerant in the air near the leak site is difficult to differentiate from the surroundings. However, by infusing into the circulating system a small amount of fluorescent dye which is soluble in the refrigerant, the dye is carried out of the system with the refrigerant, and glows brightly at the leak site when the area is swept with a UV lamp. A similar procedure can be used to locate leaks of other fluids, such as lubricant oils, fuels, heat transfer fluids or hydraulic fluids. Other UV inspection techniques use fluorescent dyes or paint to detect fissures or stress cracks in structural members. Where an inspection for leaks, cracks or fissures is conducted in confined or difficult to reach spaces, it would be advantageous to use a compact, hand-held lamp. Furthermore a compact handheld lamp is need for use in the diagnostics of vehicles where the operator of the lamp must maneuver the lamp into the tight spaces of the engine compartment of a motor vehicle.

Attempts have been made to develop compact UV lamps. For example, U.S. Pat. No. 5,050,055 to Lindsay et al., discloses a high intensity lamp portable UV lamp that is formed by a first and second housing halves fitted together and integrally formed with a handle. While the lamp is portable, the housing of the lamp is large and bulky. Moreover, the housing extends at approximately equal longitudinal portions over the handle of the lamp, making the maneuvering of the lamp in tight spaces of more difficult. U.S. Pat. No. 5,905,268 to Garcia et al. discloses is another handheld UV lamp for the detection of fluorescent material. The longitudinal dimensions of the handle and the bulb housing are nearly the same as each other, with the rear of the housing jutting out far over the handle, making the lamp bulky and difficult to maneuver within the compartment of a motor vehicle. Many other handheld UV lamps have been designed to resemble conventional flashlights. One such example is U.S. Pat. No. 5,788,364 to Cooper et al. A disadvantage of the flashlight design is that it creates a handle with a very long longitudinal axis, making the lamp difficult to maneuver within the close confines of an engine compartment.

Therefore a compact, hand-held, ultraviolet inspection lamp has not previously been developed to maneuver in compact spaces, particularly for the diagnosis of automobiles.

SUMMARY OF THE INVENTION

The present invention is a handheld UV lamp that is ergonomically designed to be compact and easily maneuverable, particularly within the housing of an engine compartment. The lamp has a housing with a grippable handle portion with a first finger indentation with an on/off trigger switch received within a recess therein, a bulb chamber portion with a filter lens, and a bulb assembly with a bulb and a reflector, the bulb assembly being positioned within the bulb chamber portion.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 6 is a rear view thereof;

FIG. 7 is a top plan view thereof;

FIG. 8 is a bottom plan view thereof;

DETAILED DESCRIPTION OF A PREFERRED EMBODIMENT

Figure 1:
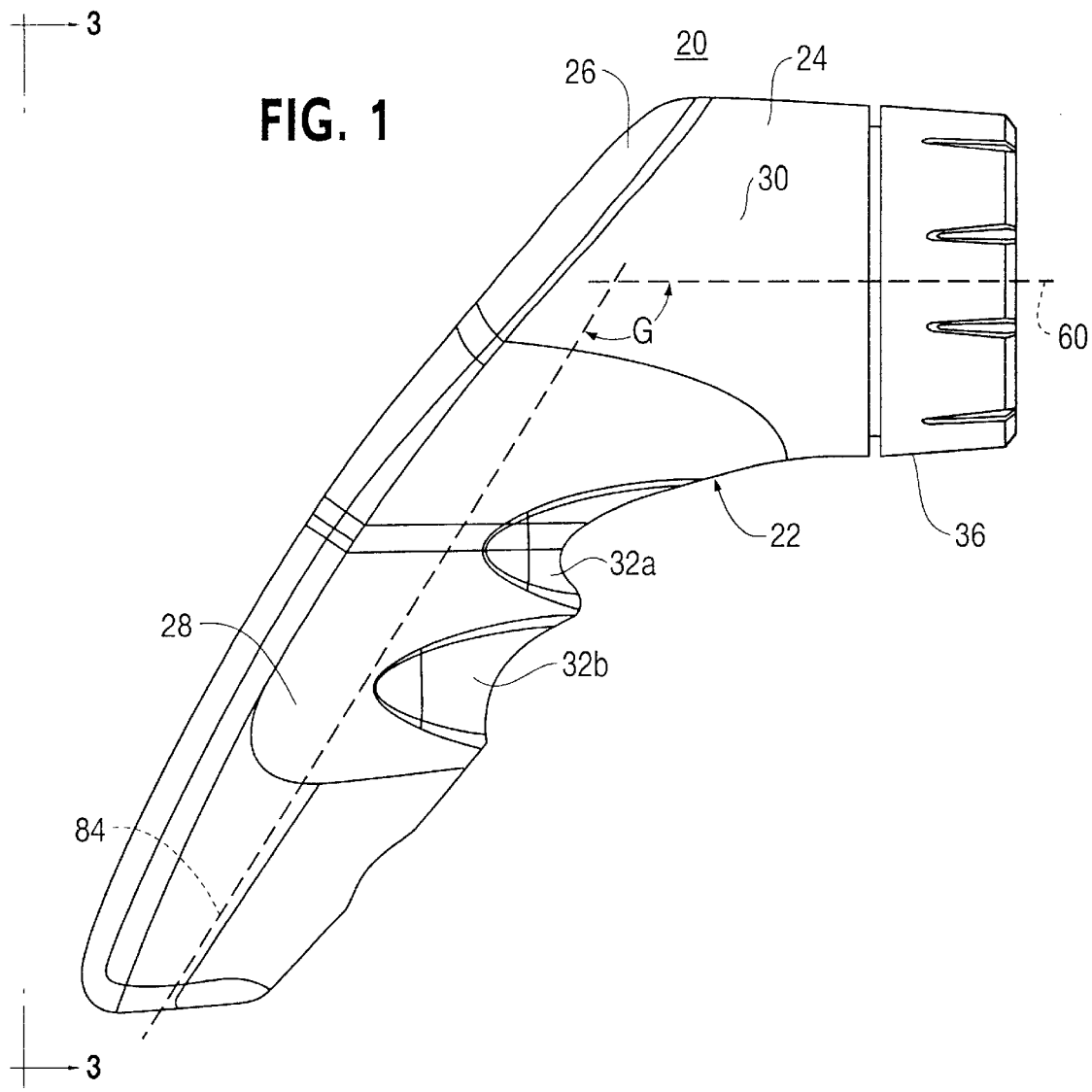
FIG. 1 is a side view of the present invention.
Figure 2:
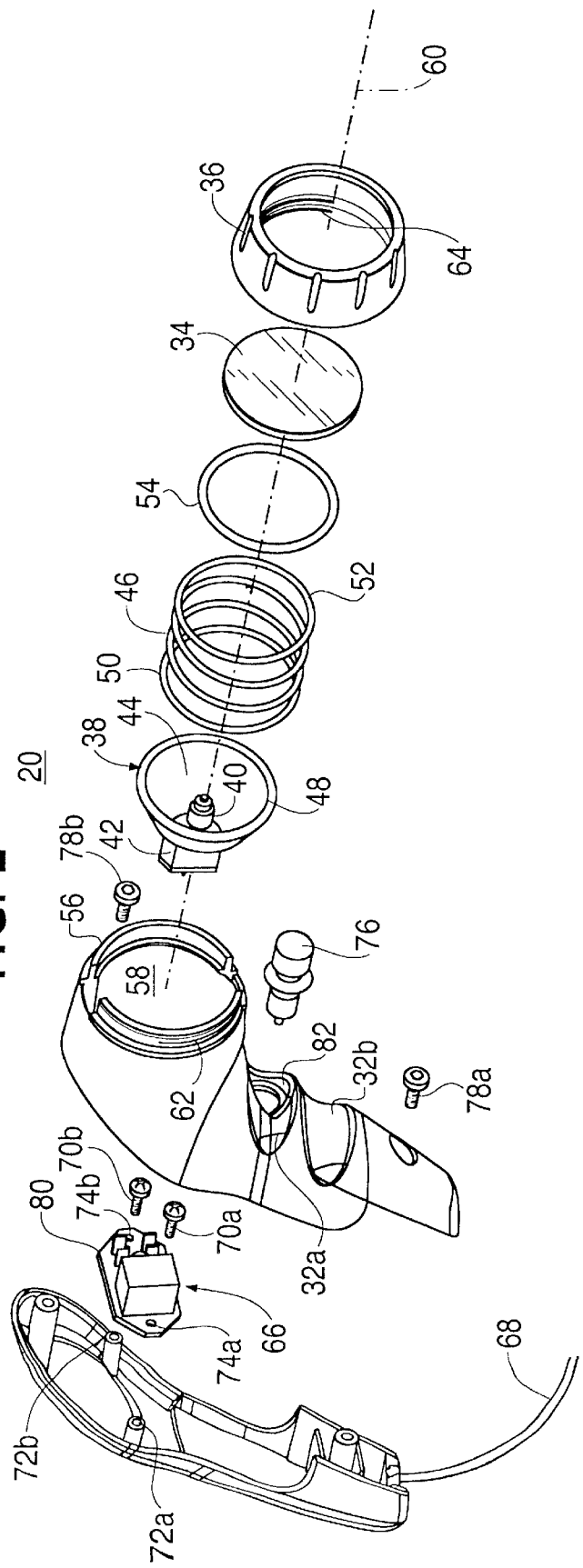
FIG. 2 is an exploded view thereof.
Figure 3:
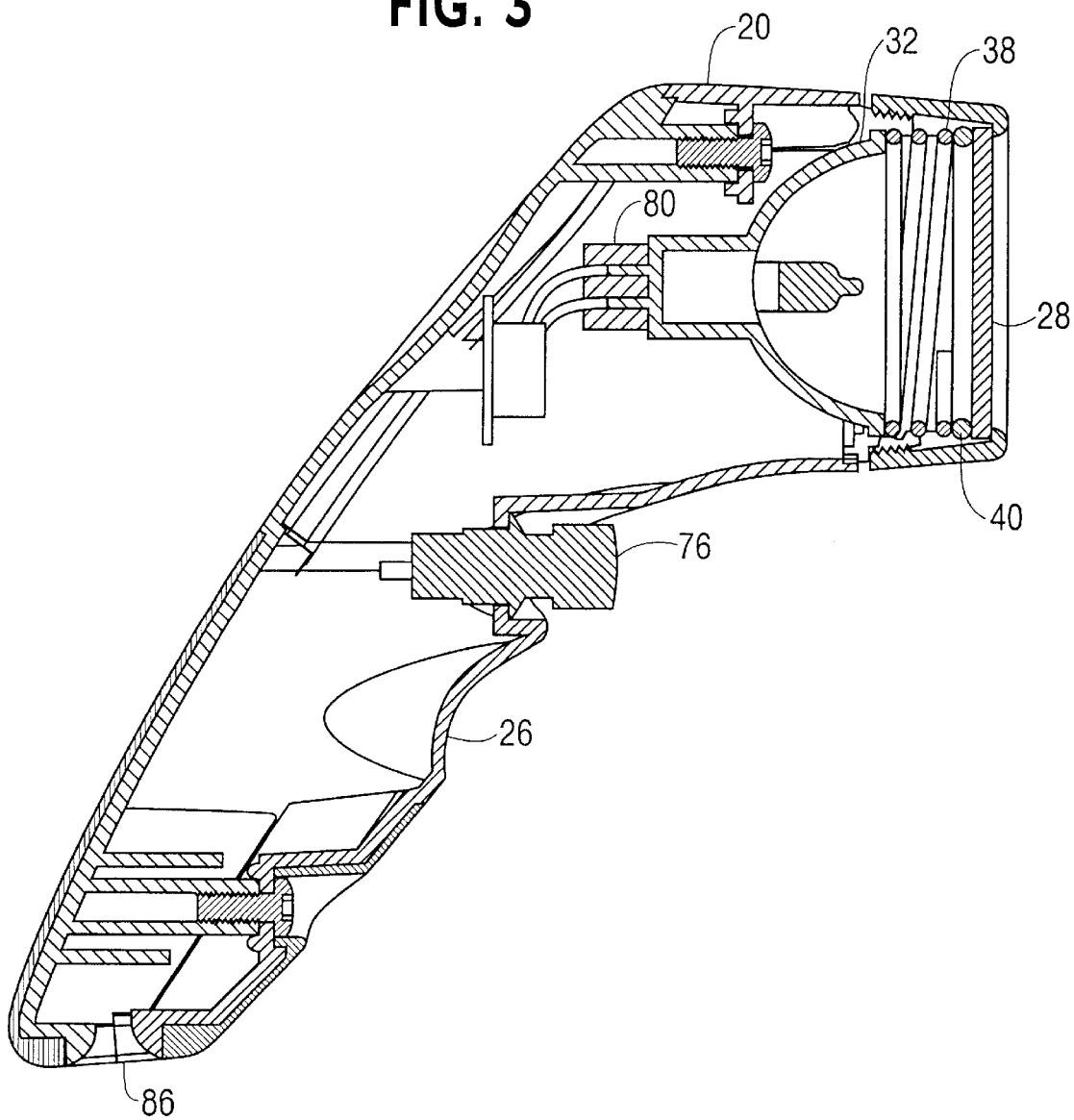
FIG. 3 is a cross-sectional view thereof.

As shown in FIG. 1 through 10, an ultraviolet light inspection device 20 includes a housing 22 having a front housing section 24 and a rear housing section 26. The housing 22 may be made of an impact resistant heat-resistant material such as a plastic or resin, for example a nylon or glass filled nylon. The rear housing section 26 releasably connects to the front housing section 24 to form the housing 22. The housing 22 includes a handle portion 28 and a bulb chamber portion 30. The handle portion 28 has finger indentions 32 to aid the grip of an operator (not shown).

Figure 4:
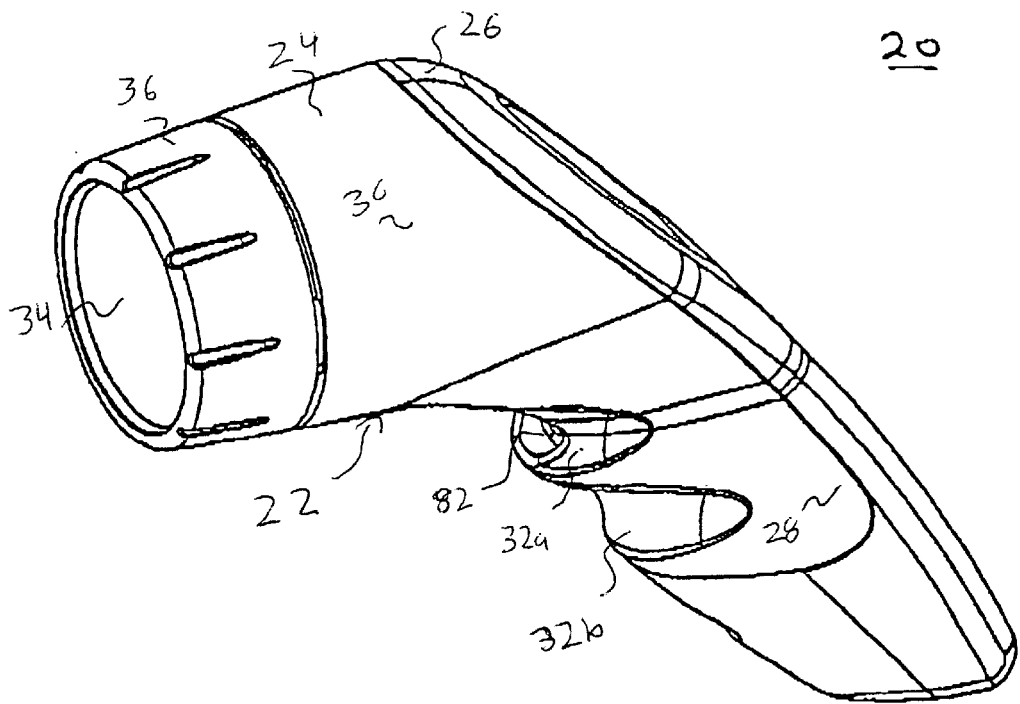
FIG. 4 is a front perspective view thereof.
Figure 5:
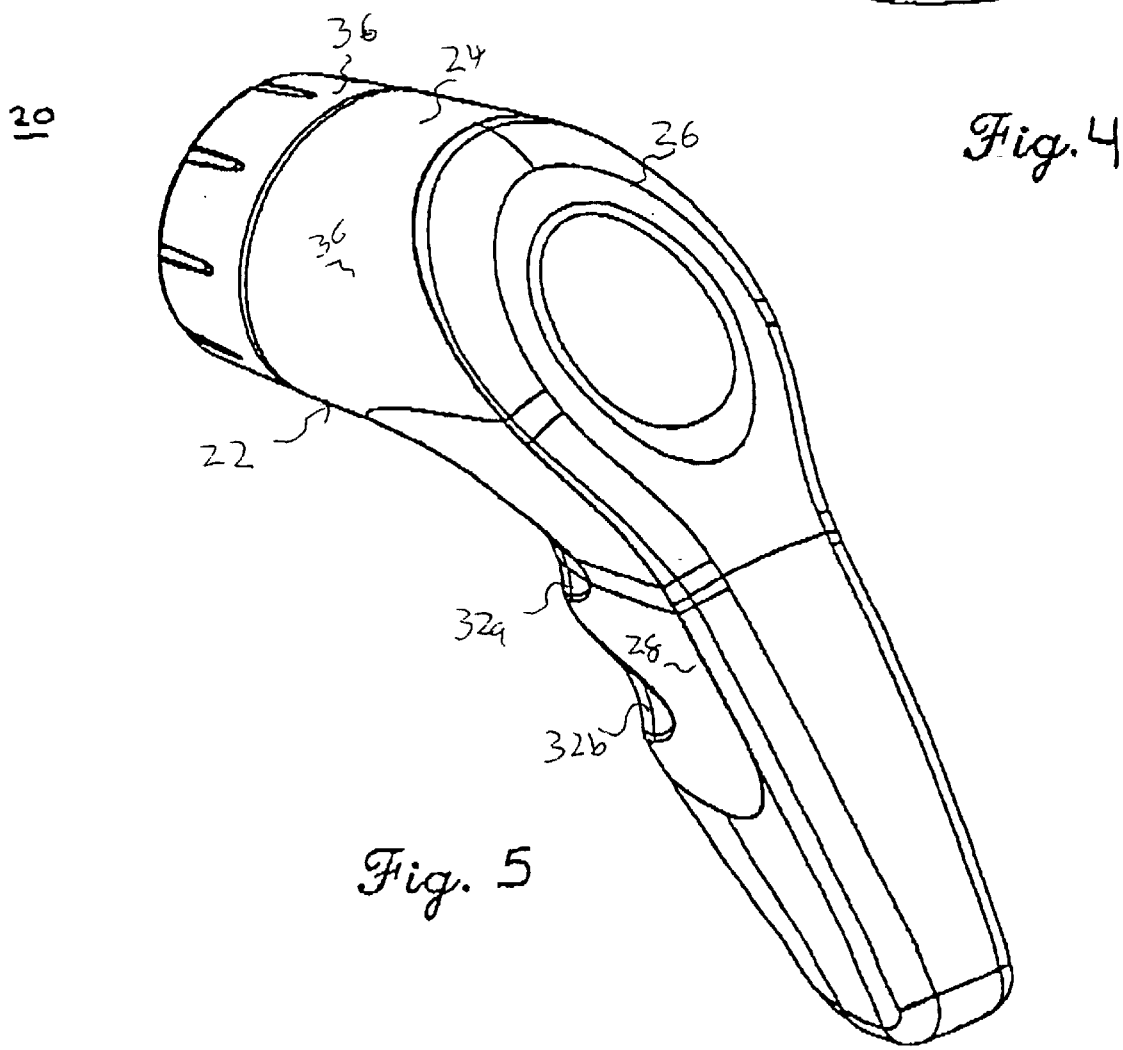
FIG. 5 is a rear perspective view thereof.
Figure 10:
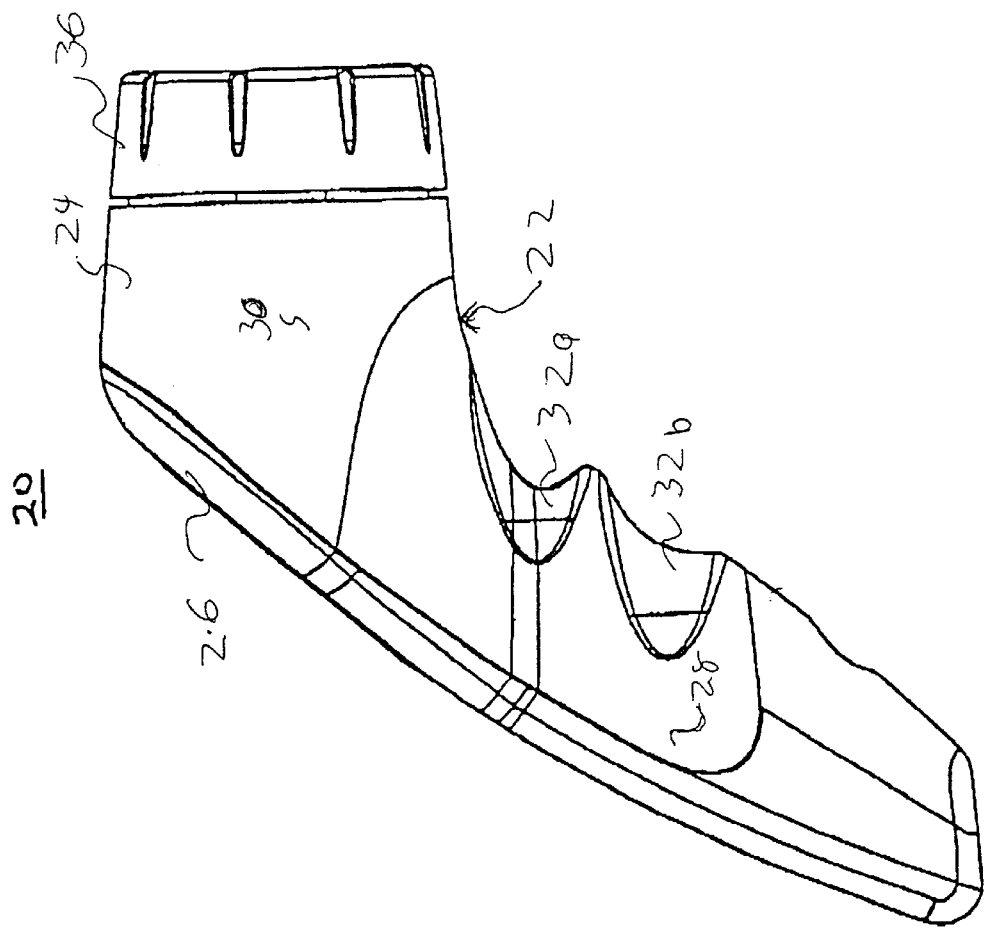
FIG. 10 is a side view thereof.
Figure 9:
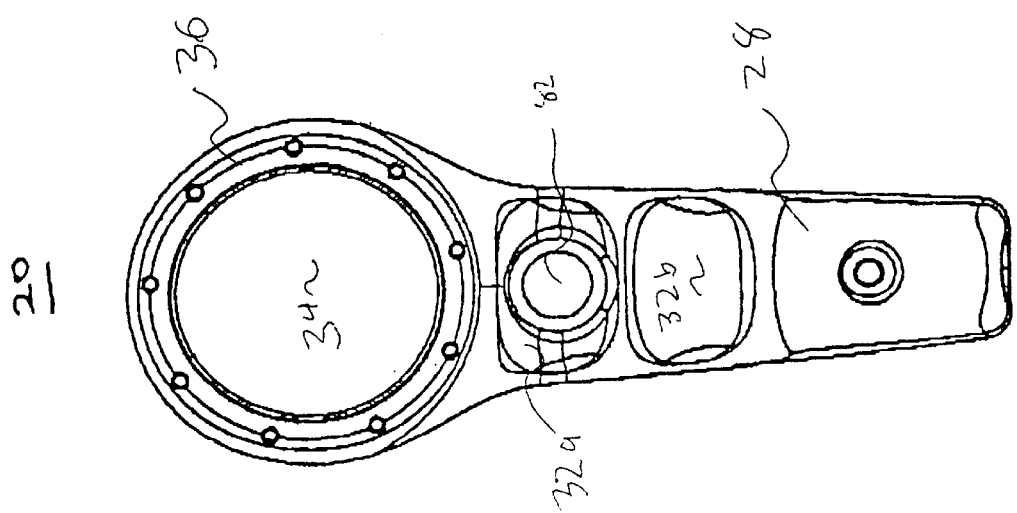
FIG. 9 is a front view thereof.

As shown in FIG. 4, the bulb chamber portion 30 includes a filter lens 34 that is retained by a retention collar 36. The filter lens 34 may be made of any materials that allows the transmission of ultraviolet light, for example between 200 and 400 nanometers. An examples of a lens is disclosed in Kalley U.S. Pat. No. 5,674,000 which is incorporated herein by reference, and which discloses a BSI lens filter NO. PS-600 that provides about 82% transmission of light that is at a wavelength of approximately 400 nm. Such lens are well-known in the art. In broader terms, the filter lens 34 is an ultraviolet filter which absorbs substantially all incident light in the visible spectrum, while transmitting a substantial portion of incident light in at least some band of the UVA spectrum. Such filters are well known and often referred to as "black light" filters. Thus, the filter absorbs light emitted from the bulb at visible and other wavelengths, but transmits ultraviolet light in the UVA spectrum.

The bulb chamber portion 30 serves as an enclosure to protect a bulb assembly 38 which includes (a) a high intensity bulb 40 for generating an ultraviolet light source, (b) an electrical pin plug 42 for receiving and supporting the bulb 40 and (c) a focusing reflector 44 having the bulb positioned therein. The bulb assembly 38 is stabilized and retained within the bulb chamber portion 30 by the force of a spring 46 which at one end 50 engages a circumferential forward lip 48 of the reflector 44 and at a second end 52 engages a flat protective ring 54 positioned adjacent the rear side of the lens 34. The bulb chamber portion includes a forward extending neck 56 having an aperture 58 to permit the transmission of light from the bulb 40 directly and upon reflectance off of the reflector 44 along a first axis 60 through lens 34. The outer circumference of the neck 56 has threads 62 which threadably receive corresponding threads 64 of collar 36 located on the interior of the collar 36. Attaching the collar 36 to the neck 56 causes compression of the spring 46 which applies a desired force against the bulb assembly 42 to retain the assembly 42 in position within the chamber 30. The spring 46 also acts to cushion the lens 34 against unintended impacts.

The power received by the bulb 40 may be modified and/or controlled by a power modifier circuit element 66 as is well known in the art. The modifier circuit element 66 through connector 80 is in electrical communication with the plug 42 for transferring modified power from an electrical cord 68 through the element 66, connector 80 and plug 42 to the bulb 40. The modifier circuit element 66 is secured to the rear housing 26 by attachment screws 70a,b which screw into orifices 72a,b of rear housing 26 through holes 74a,b of element 66. An ON/OFF momentary control switch 76 may be manipulated (triggered) by the operators forefinger to permit power to flow from the cord 68 to the bulb 40. As is well known in the art, the momentary ON/OFF switches take advantage of the halogen tungsten bulb's ability to produce intense radiation without a warm-up period. This allows a user to turn the lamp on only when the UVA illumination is wanted, limiting the time during which any heat will be generated.

The bulb 40 may be in the form of 75 watt tungsten halogen bulb although other types and power ratings of high intensity bulbs could be used. The focusing reflector 44 has a conic section shape selected for focusing the light emitted from the bulb 40. The bulb 40 is mounted such that the light source essentially encompasses the focus or foci of the reflector 44. The reflector preferably reflects the lights so that is travels substantially in the direction of the first axis 60. Suitable well known reflector shapes include hybrid conic sections selected to focus the UVA light at approximately eighteen inches from the bulb, which converges the light into a beam of sufficient intensity at convenient working distances for most UVA fluorescent inspections. The interior surface 88 of the focusing reflector 44 is preferably a highly polished to effective reflect the light from the bulb.

The front housing 24 is attached to the rear housing 26 by retention screws 78a,b. The front housing 24 has in the grip portion a pair of finger indentions 32a,b which comfortably receive the fore finger and the middle finger of the operator during use of the device 20. A recess 82 in the upper finger indention 32a receives the switch 76 for operation by the forefinger of the operator.

The handle portion 28 of the device 20 has a longitudinal second axis 84 that intersects with the first axis 60 of the bulb chamber 30 to form an interior obtuse angle gamma (G) that is preferably between about 100 and about 130 degrees in measurement. The bottom of the handle portion 28 receives the electrical cord 68 through an opening 86.

The device 20 is used in a method to detect fluid leaks in for example automobile air conditioning systems. The method involves injecting a flourescent dye into the system resulting in the dye escaping through any undesired leaks in the system. The device 20 is then maneuvered to shine ultraviolet light in various locations of the system to cause the leaking dye to fluoresce thereby identifying the location of the leak.

We claim:

1. A handheld ultraviolet inspection lamp comprising:
   a housing including:
      a front housing section and a rear housing section;
      a grippable handle portion extending from said rear housing section, said rear housing section having a surface extending in a continuous convex manner from said front housing section and in a continuous substantially planar manner to said handle portion;
      wherein said front housing section extends in a forward direction away from said handle portion; and
      wherein said handle portion includes a first finger indentation having an on/off trigger switch received within a recess therein;
      wherein said front housing section includes:
         a bulb chamber portion having a filter lens, and
         a bulb assembly disposed in said bulb chamber portion, and including a bulb and a reflector.

2. The lamp according to claim 1, wherein said bulb chamber has a first axis and said handle has a second axis, and wherein said axes intersect to form an inner obtuse angle between about 100 and 130 degrees.

3. The lamp according to claim 1, wherein said trigger switch is a momentary control switch.

4. The lamp according to claim 1, wherein said first finger is a forefinger, and said trigger switch is capable of being activated by said forefinger of the operator.

5. The lamp according to claim 1, wherein said first finger indentation is capable of receiving a forefinger of an operator.

6. The lamp according to claim 1, wherein said grippable handle portion further comprises a second finger indentation.

7. The lamp according to claim 6, wherein said second finger indentation is capable of receiving a middle finger of an operator.

8. The lamp according to claim 1, wherein said reflector has a conic shape.

* * * * *